(12) United States Patent
Nelson et al.

(10) Patent No.: US 6,726,678 B1
(45) Date of Patent: Apr. 27, 2004

(54) IMPLANTABLE RESERVOIR AND SYSTEM FOR DELIVERY OF A THERAPEUTIC AGENT

(75) Inventors: Randy Nelson, Pine Springs, MN (US); Charles L. Truwit, Wayzata, MN (US)

(73) Assignee: iSurgical, LLC, Minneapolis, MN (US)

( * ) Notice: Subject to any disclaimer, the term of this patent is extended or adjusted under 35 U.S.C. 154(b) by 0 days.

(21) Appl. No.: 09/790,982

(22) Filed: Feb. 22, 2001

(51) Int. Cl.$^7$ ................................................ A61K 9/22
(52) U.S. Cl. ................ 604/891.1; 604/502; 604/288.01
(58) Field of Search ........................ 604/890.1, 891.1, 604/500, 502, 503, 131, 151, 152, 153, 154, 245, 246, 257, 288.01, 288.02, 288.03, 288.04

(56) References Cited

U.S. PATENT DOCUMENTS

| | | | | |
|---|---|---|---|---|
| 3,310,051 A | * | 3/1967 | Shulte | ........................ 604/175 |
| 3,923,060 A | * | 12/1975 | Ellinwood, Jr. | .......... 604/891.1 |
| 4,710,177 A | * | 12/1987 | Smith et al. | ................. 604/185 |
| 5,643,207 A | * | 7/1997 | Rise | ........................ 604/93.01 |
| 5,836,935 A | * | 11/1998 | Ashton et al. | ........... 604/891.1 |
| 5,951,263 A | * | 9/1999 | Taylor et al. | ................ 417/356 |

* cited by examiner

*Primary Examiner*—Edward K. Look
*Assistant Examiner*—John K. Fristoe, Jr.
(74) *Attorney, Agent, or Firm*—Schwegman, Lundberg, Woessner & Kluth, P.A.

(57) ABSTRACT

There is disclosed method and apparatus for retaining a reservoir for a therapeutic agent between the scalp and cranium of a subject, including providing a deformable pouch or rigid cylinder for dispensing the therapeutic agent from the reservoir to a location in the body of the subject. In one embodiment, a pump is used to pump the agent from the reservoir to the location in the subject's body. In another example embodiment, there is provided method and apparatus for forming at least one cavity in the cranium of the subject, and placing at least a portion of the pump in the cavity. Power is applied to the pump in a variety of ways.

21 Claims, 17 Drawing Sheets

_US 6,726,678 B1_

IMPLANTABLE RESERVOIR AND SYSTEM FOR DELIVERY OF A THERAPEUTIC AGENT

TECHNICAL FIELD OF THE INVENTION

This invention relates generally to the field of medicine, and more particularly to implantable devices for delivering therapeutic agents to a body.

BACKGROUND OF THE INVENTION

Localized drug therapy has been shown to be successful for chronic pain treatment and chemotherapy for spinal disorders using less drugs and without the potential adverse effects of a systemic dosage. Pumps for abdominal implant have been designed to dispense drugs as either continual dosage through a constant pressure, non-electrical means or as programmable, periodic dispensing through the use of an electrically driven pump and constant pressure reservoir.

More recently, the value of localized drug therapy for neurological disorders has been identified. Existing pumps, while potentially providing the therapeutic advantages of implantable infusion pumps, are large and are implanted abdominally. Such pumps if used will require a catheter tunneled from the abdominal implant site, through the neck to an entry site in the head, and then to the localized treatment site.

Present electrically powered pumps use primary (non-rechargeable) batteries as their power source. When the battery is depleted in these devices, the complete assembly must be removed and replaced. Rechargeable batteries have been used in previous implant devices including earlier pacemakers and present day artificial hearts and left ventricular assist devices (LVAD's). Artificial hearts and LVAD's require the use of an external power source due to the high power demand of the pumping system that would deplete an internal battery quickly. They also use a rechargeable battery to provide power for a patient when external power is not appropriate, such as when taking a shower or bath. Earlier pacemakers used a nickel cadmium rechargeable battery system that relied on the patient to recharge transcutaneously on a periodic basis.

SUMMARY OF THE INVENTION

According to one aspect, the present invention provides method and apparatus for retaining a reservoir for a therapeutic agent between the scalp and cranium of a subject. According to another aspect, there is provided method and apparatus for dispensing the therapeutic agent from the reservoir to a location in the body of the subject. According to yet another aspect, there is provided method and apparatus for pumping the agent to the location in the subject's body with a pump. According to still another aspect, there is provided method and apparatus for forming at least one cavity in the cranium of the subject, and placing at least a portion of the pump in the cavity. According to still other aspects of the method and apparatus, power is supplied to the pump. These and other aspects of the invention are described below.

DETAILED DESCRIPTION

Figure 1A:
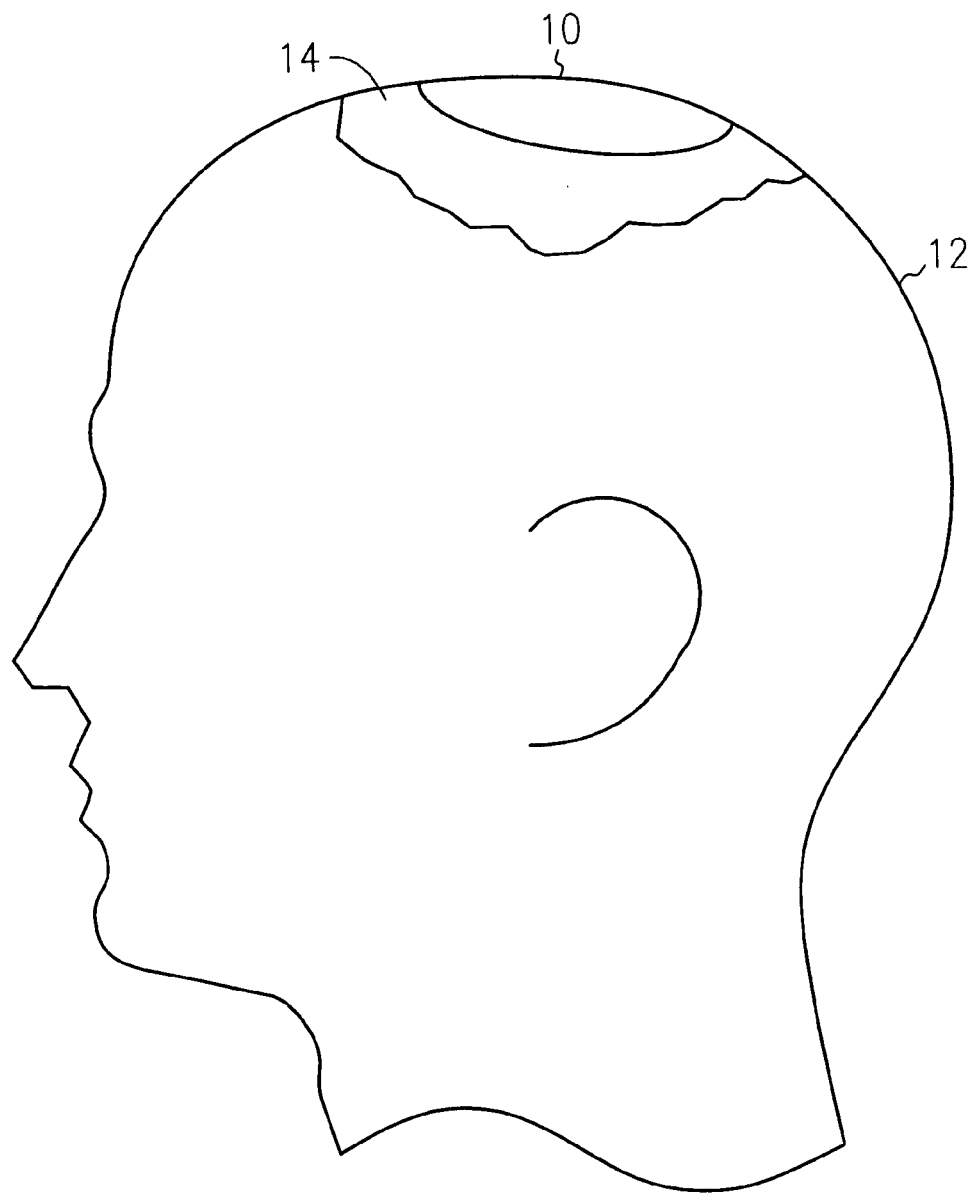
FIGS. 1A and 1B show therapeutic agent reservoirs according to certain example embodiments of the invention.

In the following detailed description of sample embodiments of the invention, reference is made to the accompanying drawings which form a part hereof, and in which is shown by way of illustration specific sample embodiments in which the invention may be practiced. These embodiments are described in sufficient detail to enable those skilled in the art to practice the invention, and it is to be understood that other embodiments may be utilized and that logical, mechanical, electrical and other changes may be made without departing from the spirit or scope of the present invention. The following detailed description is, therefore, not to be taken in a limiting sense, and the scope of the present invention is defined only by the appended claims.

EXAMPLE METHODS

There is described below a number of example embodiments of the invention relating to dispensing a therapeutic agent from an implanted reservoir to a treatment site in a subject's body. According to a first example embodiment of the methods of the invention, a reservoir for a therapeutic agent is retained between the scalp and cranium of a subject. In another embodiment, the reservoir is positioned proximate a subject's spinal. In another embodiment, the reservoir is hermetically sealed, for example with a metallic substance, such as a metal foil or hard casing.

In yet another embodiment, the agent is stored in a reservoir having one or more bladders or pouches adapted to occupy a substantially planar space. Yet still another example embodiment of the methods of the invention provides that the reservoir is deployed in the space between the scalp and cranium using one or more deployment lines connected at or near the edge of the reservoir that when pulled deploy the reservoir in a desired position.

In yet another example embodiment, where there is more than one bladder, and the bladders are connected with at least one fluid conduit allowing therapeutic agent to flow from one bladder to the other.

According to another embodiment of the methods of the invention, the reservoir is refilled using a hypodermic needle that is inserted transcutaneously and into a refill port on the reservoir or connected to the reservoir that is adapted to receive the needle.

In yet another example embodiment, the reservoir is substantially planar, and the port is oriented so that the needle is inserted along a line that is generally parallel to the plane of the reservoir. Where, in one example embodiment, the reservoir is substantially planar, the port is oriented so that the needle is inserted along a line that is generally perpendicular to the plane of the reservoir. In another embodiment, the port is connected to the reservoir through a fluid conduit, and the port position spaced apart from the reservoir, for example behind the ear, with the conduit tunneled under the scalp.

In another example embodiment, the reservoir is substantially planar, and the edges of the housing of the reservoir taper from a smaller thickness at the edge to a greater thickness away from the edge.

Still another example embodiment of the methods of the invention provides for holding one or more different therapeutic agents in one or more additional implanted reservoirs, and dispensing the different agents from each reservoir.

In one more example embodiment of the methods of the invention, the reservoir is retained subcutaneously between the subject's galea aponeurotica and cranium so that the reservoir outline is imperceptible to a casual observer. In this case or others the reservoir is anchored by suturing to the subject's galea or other tissue.

Where the reservoir is a pouch, one embodiment by example provides that the pouch is held dimensionally fixed on all axes except one. In another example embodiment, the pouch is formed at least in part with a silicone or polymer.

In a further embodiment, wherein the reservoir is a pouch, and when the reservoir is full, the pouch is confined by a solid surface such as the inside of an outer hermetic enclosure or a molded plastic restrainer.

In a still further embodiment, one end of the reservoir has a fixed dimension and contains an outlet port and a filling port, with the opposing end having a non-fixed dimension and is activated by a push rod or piston mechanism to predictably collapse the pouch while pushing the therapeutic agent out under constant pressure.

In yet still another embodiment, a screw or impeller pump is located at the fixed end of the reservoir and withdraws the agent from the reservoir. In one such example embodiment, the reservoir is a pouch and the agent is pumped from the pouch, and the pouch collapses as it is emptied, maintaining the appropriate pressure/volume ratio inside the hermetic enclosure and thereby eliminating a vacuum within the reservoir. Another example embodiment provides that the reservoir is a solid cylinder with the outlet port or valve mechanism located on one end of the cylinder, and the opposing end is fitted with a push rod/sealing piston to retain the therapeutic agent and to force the agent through the outlet port. Another embodiment provides that after an infusion cycle, the drive or stepper motor reverses enough to release pressure on the therapeutic agent chamber and to maintain a slight negative pressure in relation to that of the surrounding anatomy.

In one example embodiment of the methods, the reservoir is a square or round hollow, rigid tube coiled to maintain a flat or specifically shaped profile of minimum surface area, and the reservoir is filled through an inflow valve located at or near one end of the tube, and the outflow port is located at the opposite end of the tube from the filling port.

According to another example embodiment the reservoir is formed from a collection of multiple reservoirs, connected by tubing, designed to provide a flexible or contoured implant device shape that can form to the shape of the subject's cranium, and wherein the reservoir is filled by syringe through a fill port attached to one of the reservoir sections and thereby fills all reservoir sections through the connected tubing. In another embodiment, the reservoir(s) is contoured to the shape of a subject's lower back.

In still another embodiment, a pump that will pump agent from the reservoir is located in a manner that provides complete drainage of all reservoirs sections during a therapy cycle.

According to yet another example embodiment of the methods the reservoir is refilled through a sealed silicone portal that is accessed by a needle through the skin.

According to still another embodiment, the therapeutic agent is dispensed from a reservoir under the scalp to a location in the brain of the subject. In another embodiment, the therapeutic agent is dispensed from a reservoir located in the soft tissue of the lower back to a location in the spine of the subject. Such dispensing is done in one example embodiment based on programmed parameters. Such programmed parameters are for example telemetered transcutaneously. Further, information may be telemetered transcutaneously from a pumping device to a device outside the subject's body.

In yet another embodiment still, agent is dispensed using a fluid conduit with a proximal end coupled to receive agent from the reservoir and a distal end positioned in the brain of the subject.

The therapeutic agent is thus, in this example, dispensed by pumping it to the location in the subject's body with a pump, that is in one example embodiment selected from the group of: a screw, impeller, diaphragm, or piston type pump. In yet still another example embodiment, the pump is a screw or impeller type motor driven by a stepper or microstepper motor that is accurately controlled to regulate the dosage volume by number of rotations of the screw or impeller. Still another embodiment provides that the pump is a diaphragm pump or piston pump that controls dosage volume by change in volume per stroke multiplied by the number of strokes. In one embodiment, the pump is a micromachine device or an ultrasonic piezoelectric device. For example, a pump such as described in "A High-Performance Silicon Micropump for an Implantable Drug Delivery System", D. Maillefer, et al. MEMS '99 conference. Or, a pump such as that described in "Piezoelectric Flexural-Traveling-Wave Pumps". JPL New Technology Report NPO-19737. National Aeronautics and Space Administration.

In still other embodiments, the outflow of agent from the reservoir is controlled using a first valve to regulate the inflow and a second valve to regulate the outflow.

Yet another embodiment provides that the inflow valve is a mechanical valve displaced by the refill needle. In one example embodiment, the inflow valve is an electronically controlled valve that is activated by an external device at the time of filling, and/or the outflow valve is electronically controlled and timed to the outflow cycle of the pump. In this arrangement, for instance, the outflow valve is a normally closed valve located at the distal end of a catheter carrying the therapeutic agent to the location in the subject's body, and when therapeutic agent delivery is required, the valve is electrically opened and remains open for a programmed period of time.

According to yet one more embodiment, the conductors for the valve are embedded in the sidewall of the catheter.

In still another embodiment, the output valve is located at a discharge port of the pump device, and opened electrically.

In still another arrangement, there is provided a closed loop sensory mechanism that determines when to deliver a dosage of therapeutic agent and how much therapeutic agent dosage is appropriate.

Yet another example embodiment provides for forming at least one cavity in the cranium of the subject, and placing at least a portion of the pump in the cavity.

Yet more example embodiments provide for positioning the pump or electronics inside the body of the subject at a location other than the top of the head of the subject, or under the skin behind the ear of the subject, or in the chest region of the subject.

In still more embodiments, power is transmitted to the pump transcutaneously, or an implanted power source is retained within the subject's body, wherein the power source powers the pump, and for example the power source is rechargeable. Such rechargeable power source is a rechargeable battery or storage capacitor. The rechargeable power source is recharged in this embodiment, for example, by transcutaneously transmitting power to the power source.

Still other embodiments provide that the power source is integral with electronic circuitry used to control the pump.

In some operational modes for example, the therapeutic agent is pumped when an external power source is placed over the site of the pump.

The methods of the invention further provide in one example arrangement for forming at least one cavity in the cranium of the subject, and placing at least a portion of the power source in the cavity.

In some example configurations, the power source is positioned inside the body of the subject at a location other than the location of the pouch and/or pump, for example positioning the power source under the skin behind the ear of the subject, or in the chest region of the subject.

In still more example embodiments, one or more electronic components are adapted to control the dispensing of therapeutic agent from the reservoir to the subject's body. Such electronic components in some example configurations are contained in a hermetically sealed container suitable for long term human implant. Such a container is, for example, constructed of one or more materials from the following group: titanium and stainless steel.

Further, in yet still more example embodiments, the components or the pump are enclosed in a fluid-tight enclosure and all components and connections are hermetically sealed against potential moisture related failures.

In addition, in another example configuration, at least one cavity is formed in the cranium of the subject and at least portions of the components are kept in the cavity.

In yet more example embodiments of the methods, more than one cavities or burrholes are formed in a subject's cranium, and at least a portion of a pump is retained in one cavity and at least a portion of a power source for the pump in the other cavity.

Yet another example embodiment provides that electronic circuitry operates the pump based on programmed parameters.

An external device is provided on one example embodiment to telemeter signals into and out of the electronic circuitry. In such an example embodiment, the external device reprograms the electronic circuitry as necessary, and collects and displays data as transmitted from the implantable device. Further, the external electronic device in some embodiments signals the electronic circuitry to cause an extra dose of therapeutic agent to be delivered upon demand by an operator. In some example configurations, the bidirectional transmitting provides signals to activate the circuitry within the implant device and relay status information from the circuitry to outside the subject's body. Such signals include in some example cases starting energy and signal transmission either automatically by proximity of the external device to the implanted device or by a control activated by an operator.

To provide for hermetic operation, in some example embodiments the electronic circuitry is enclosed in a fluid-tight enclosure and all electrical components and connections are hermetically sealed against potential moisture related failures.

In still yet another example embodiment, therapeutic agent is pumped using a pump and power source, and further wherein the pump and power source are housed integral to the pump and reservoir. In yet another configuration, there is included a pump and power source, and further the power source is located remotely from the reservoir. Such pump or power source are, in some example cases, implanted in the subject's body.

According to one more example embodiment, single or multiple conductors carry power from the power source to the pump, and the conductors are encased in a biocompatible flexible material, and the biocompatible material is selected from the group of: silicone or polyurethane.

In still one more example embodiment, the conductors are permanently attached to the pump and electronic components for controlling the pump in a manner that allows them to be disconnected. In one such embodiment, the wires are attached permanently to the pump. In another embodiment, they are attached permanently to the electronic power source.

Thus there has been described above various example methods for storing and dispensing a therapeutic agent from a subject's body. These methods are not limited to any particular apparatus. However, example apparatus are illustrated below.

EXAMPLE APPARATUS

Figure 1B:
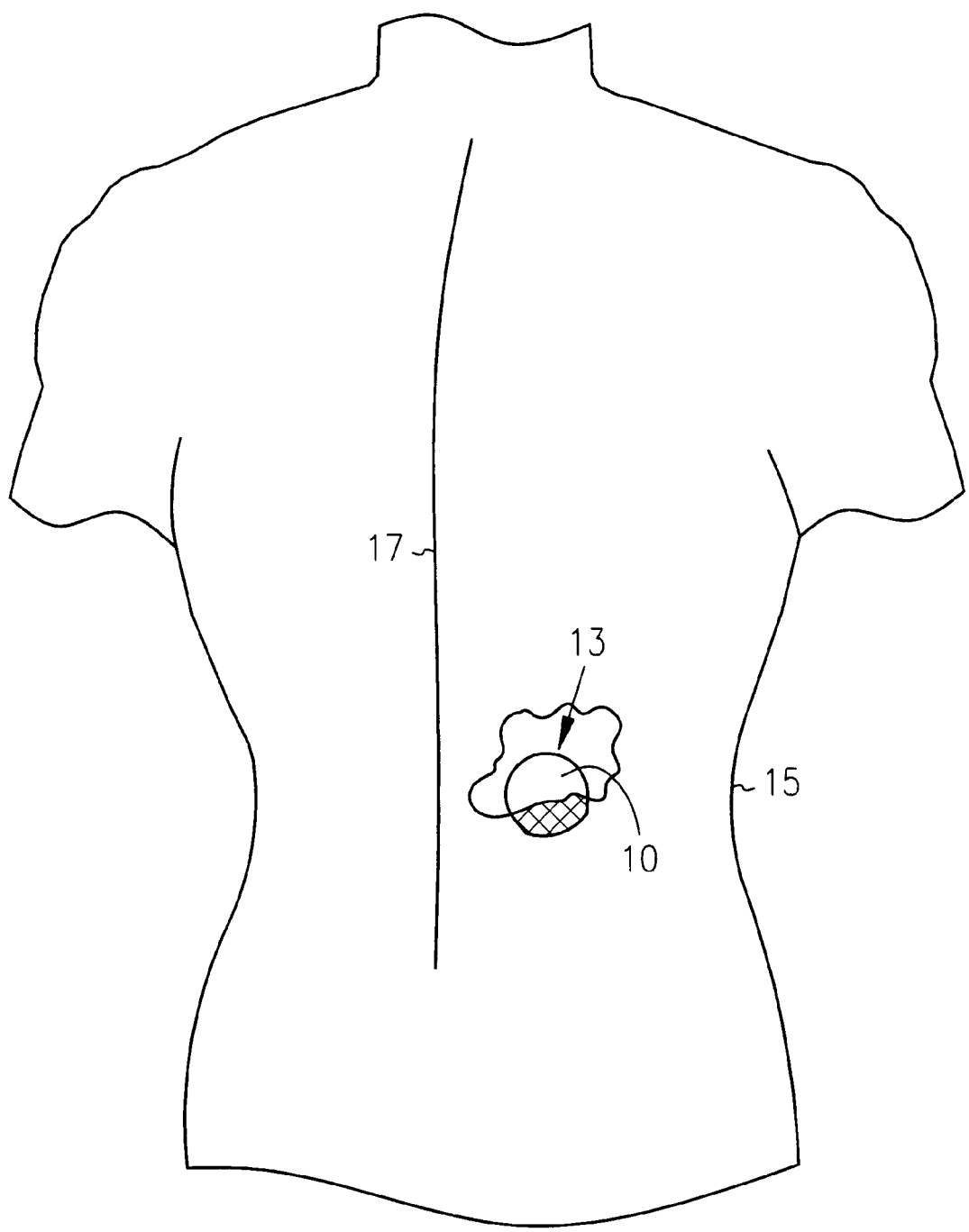

The present invention provides a number of example apparatus relating to dispensing a therapeutic agent from an implanted reservoir to a treatment site in a subject's body. According to a first example embodiment of the apparatus shown in FIG. 1A, there is provided a reservoir 10 for a therapeutic agent. In one example embodiment, the reservoir 10 is adapted to be implanted between the scalp 12 and cranium 14 of a subject. In another embodiment shown in FIG. 1B, the reservoir 10 is adapted to be implanted under the skin 15 in the soft tissue 13 of the back near the spine.

In one embodiment, a housing for the reservoir is adapted or contoured to conform to the anatomical features of the back in the area in which the implant of the housing is sought to be made.

Figure 2:
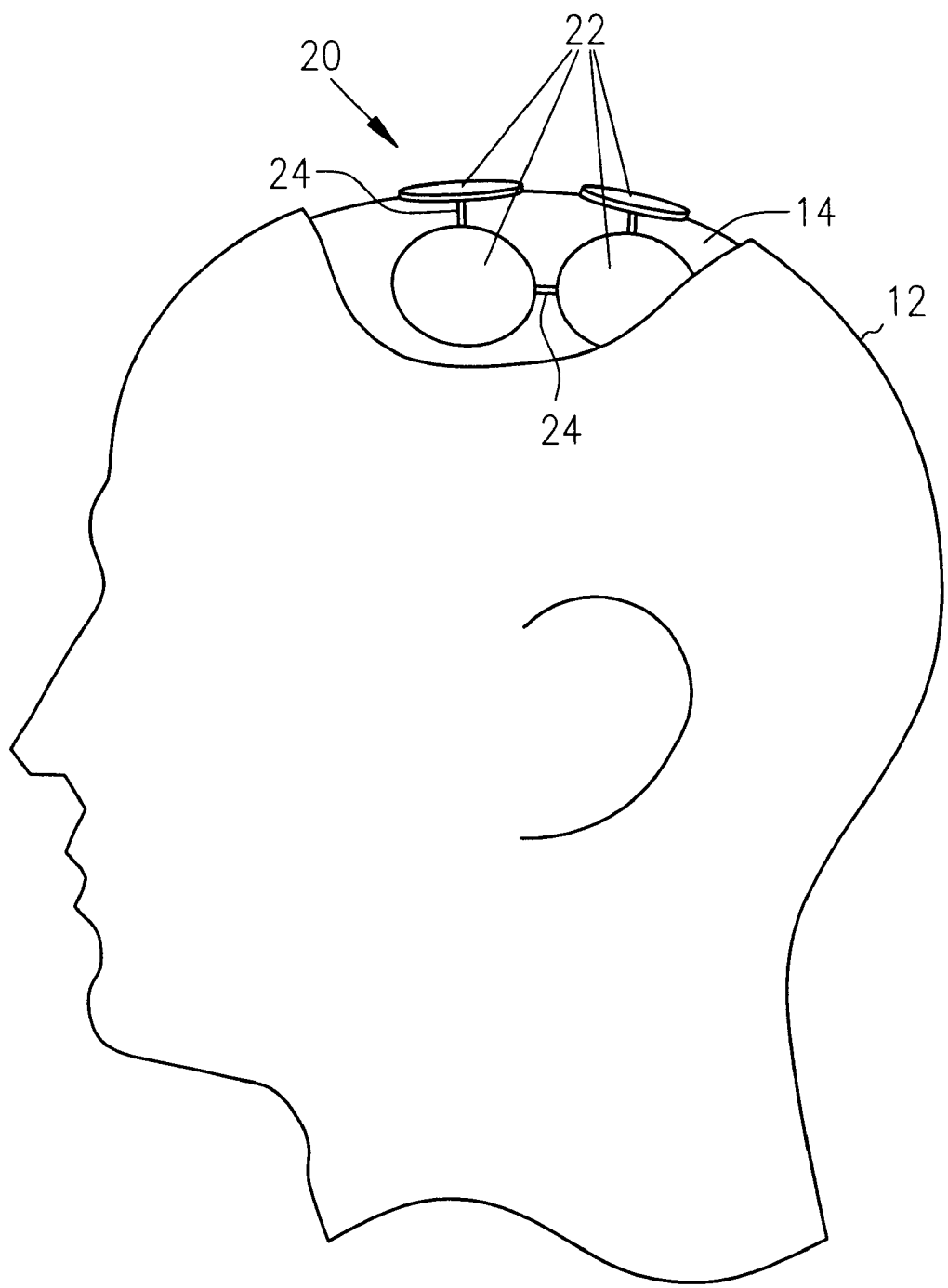
FIG. 2 shows a multiple reservoir system according to one embodiment of the invention.

In yet another embodiment shown in FIG. 2, the agent is stored in a reservoir 20 having one or more bladders or pouches 22 adapted to occupy a substantially planar space between the scalp 12 and cranium 14. According to one example embodiment shown above in FIG. 2, the reservoir is formed from a collection of multiple reservoirs or reservoir sections, connected by tubing 24, designed to provide a flexible or contoured implant device shape that can form to the shape of subject's skull, and wherein the reservoir is filled by syringe through a fill port attached to one or more of the reservoir sections and thereby fills all reservoir sections through the connected tubing 24. In still another embodiment, the reservoir sections are interconnected in a manner that provides complete drainage of all reservoirs sections prior to refill.

In another example embodiment, the pouch 22 is formed at least in part with a silicone or polymer.

According to yet another example embodiment of the apparatus the refill port is a sealed silicone portal that is accessed by a needle through the subject's skin.

Figure 3A:
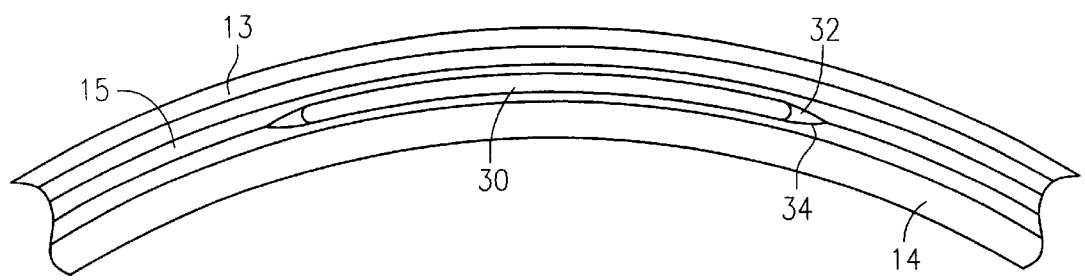
FIGS. 3A and 3B show a side view of a reservoir housing according to one example embodiment of the invention.
Figure 3B:
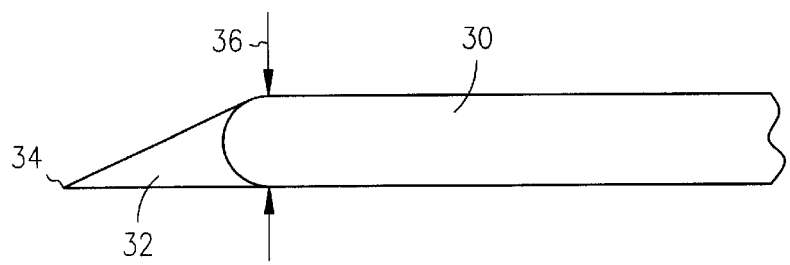

Yet still another example embodiment illustrated in FIG. 3A shows a reservoir 30 deployed in the space 16 between the scalp and cranium 14. More particularly in one example embodiment the reservoir 30 is retained subcutaneously between the subject's galea aponeurotica 15 and skin 13 so that the reservoir outline is imperceptible to a casual observer. In this case or others the reservoir is anchored by suturing to the subject's galea. In another example embodiment also shown in FIG. 3A and in FIG. 3B, the reservoir 30 is substantially planar, and the edges 32 of the reservoir taper from a smaller or feathered thickness 34 at the edge to a greater thickness 36 away from the edge.

Figure 4:
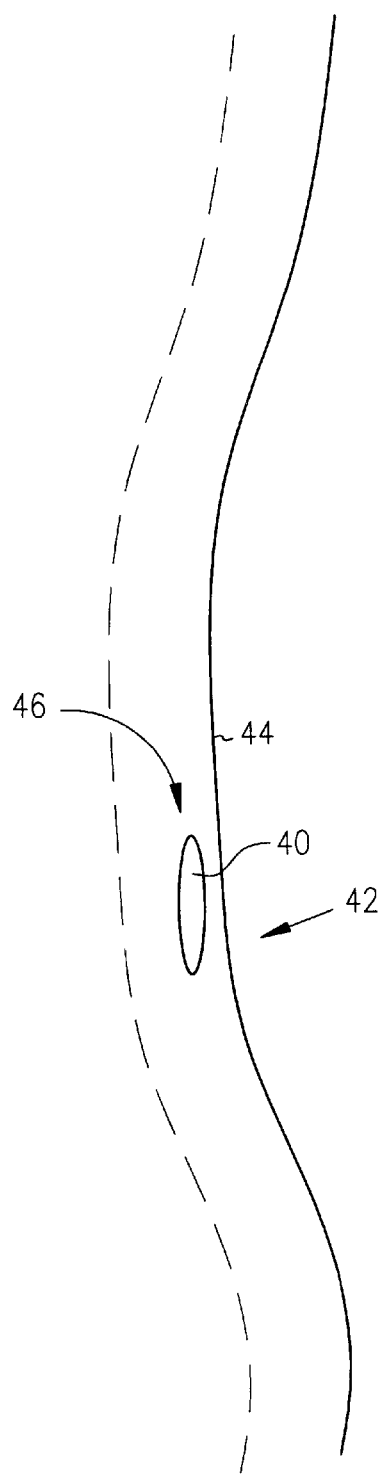
FIG. 4 shows a reservoir implanted in the back according to one embodiment of the invention.

Referring to FIG. 4, there is illustrated in one example embodiment of the invention a reservoir housing 40 implanted under skin 44 in the soft tissue 44 of the lower back 42 of a subject, wherein the reservoir housing 40 has a low profile or planar configuration adapted to fit in the soft tissue of the lower back. Alternatively, the profile or configuration can be adapted to other locations on the back or other portions of the body.

Figure 5:
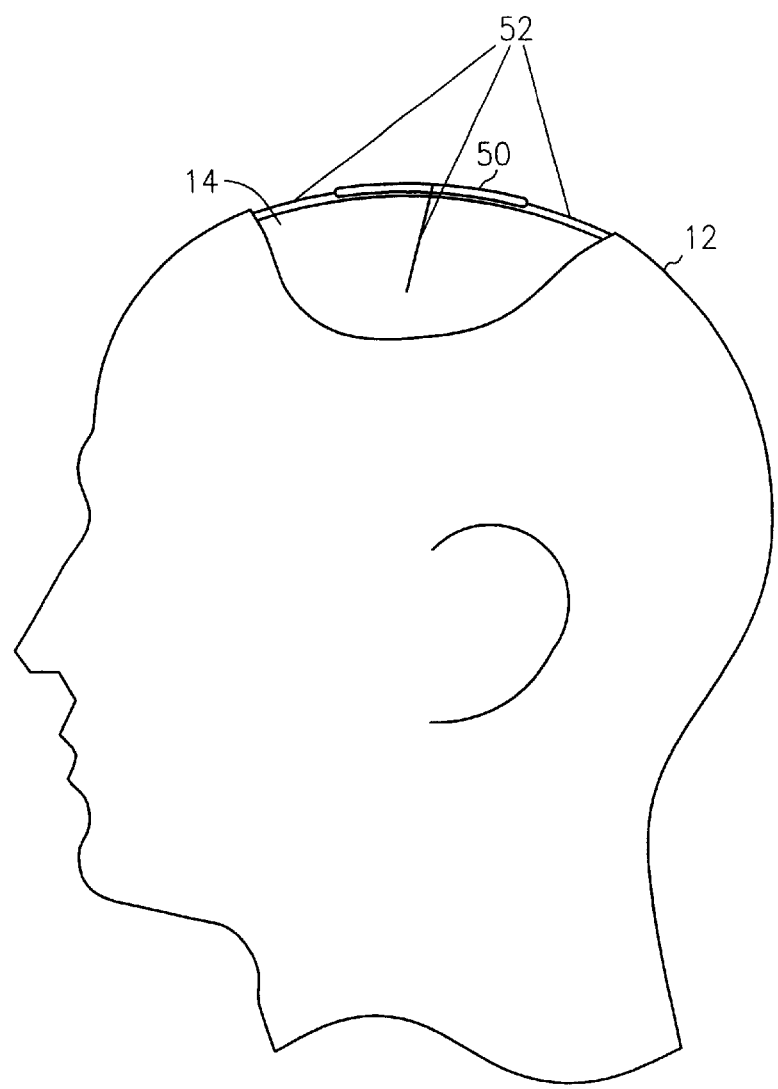
FIG. 5 shows a reservoir deployment system according to one embodiment of the invention.

As shown in FIG. 5, one or more deployment lines 52 are connected at or near the edge of the reservoir 50 such that when pulled deploy the reservoir 50 in a desired position. The reservoir is, in one example embodiment, adapted so that it conforms to the shape of the skull, for instance with a seam between bladders running along the crest or longitudinal center ridge of the cranium.

Figure 6:
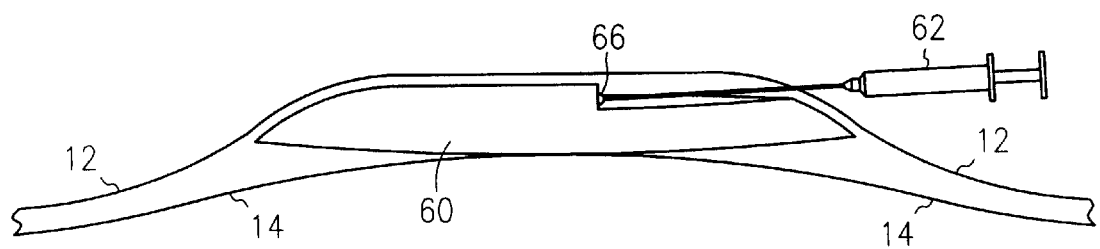
FIG. 6 shows a reservoir refill system according to one embodiment of the invention.
Figure 7:
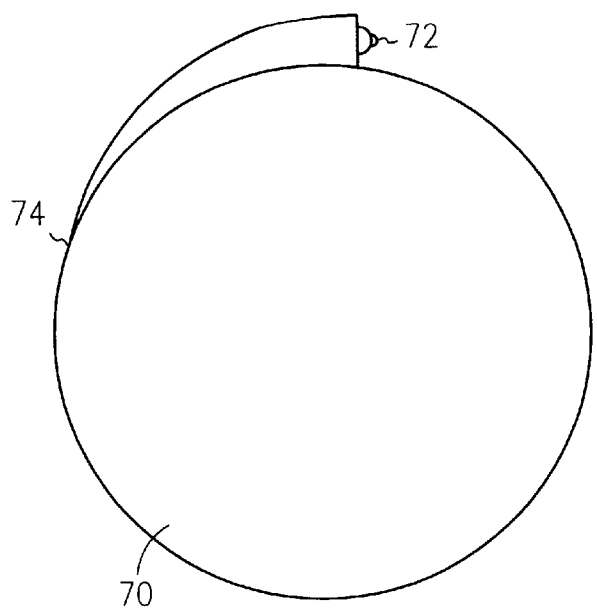
FIGS. 7 and 8 show a reservoir refill systems according to example embodiments of the invention.
Figure 8:
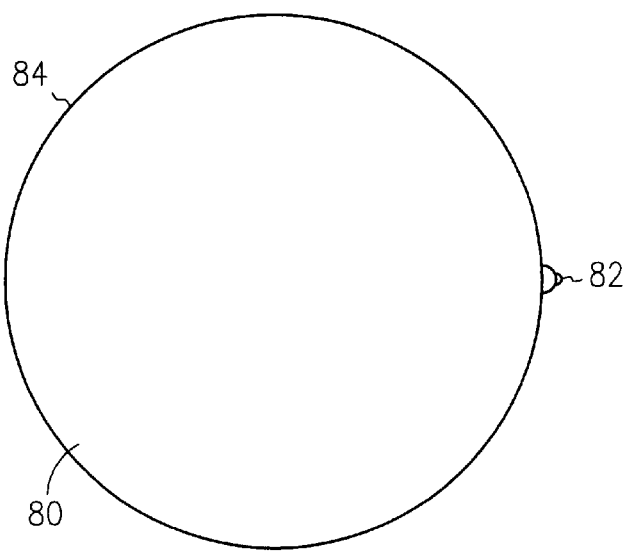
Figure 8:
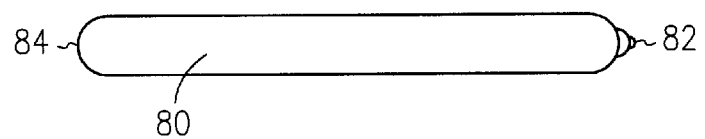

According to another embodiment of the apparatus of the invention illustrated in FIG. 6, the reservoir 60 is refilled using a hypodermic needle 62 that is inserted through the scalp or skin 12 and into a refill port 66 on the reservoir 60 adapted to receive the needle. In yet another example embodiment, the reservoir is substantially planar, and the port is oriented so that the needle is inserted along a line that is generally parallel to the plane of the reservoir. Where, in yet another example embodiment, the reservoir is substantially planar, the port is oriented so that the needle is inserted along a line that is generally perpendicular to the plane of the reservoir. As illustrated in FIG. 7, a port 72 may be located along the perimeter 74 of a reservoir 70. In FIG. 8, a port 82 is illustrated positioned on the side 84 of reservoir 80.

Figure 9:
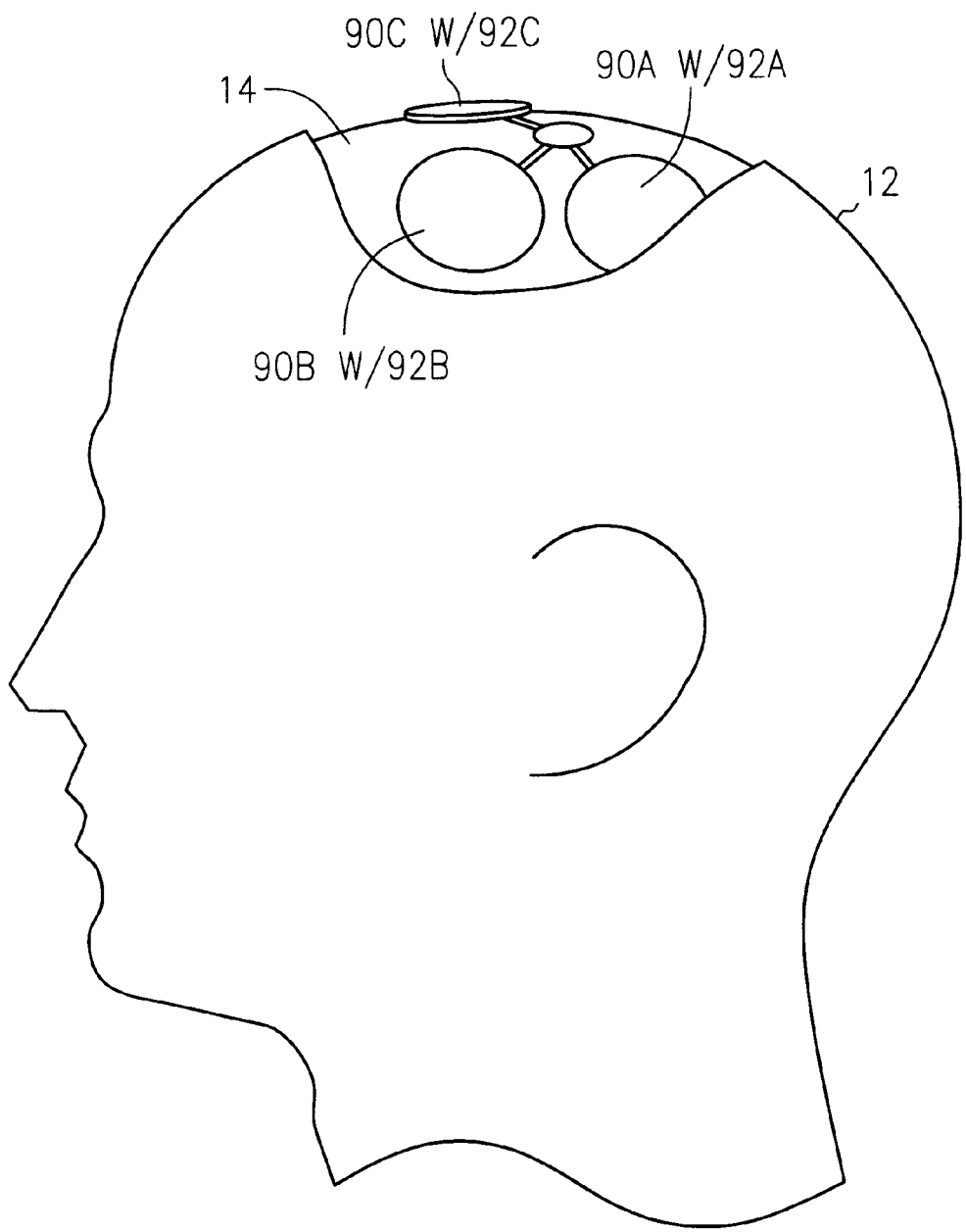
FIG. 9 shows a multiple reservoir system with multiple therapeutic agents stored therein according to one embodiment of the invention.

Still another example embodiment illustrated in FIG. 9 provides for holding one or more different therapeutic agents 92a, 92b and 92c in one or more additional reservoirs 90a, 90b and 90c which are implanted under the scalp 12, and dispensing the different agents from each reservoir.

Figure 10:
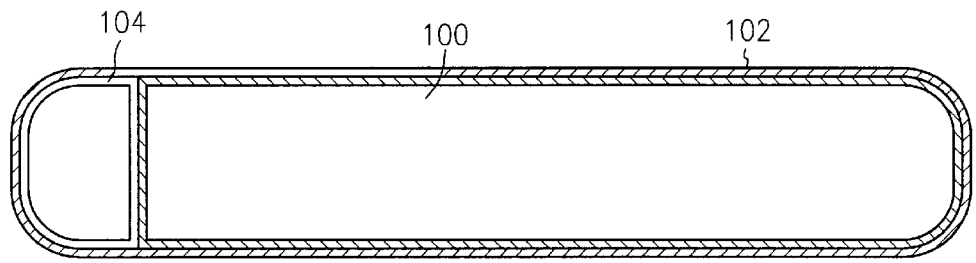
FIGS. 10–15 show various reservoir systems according to various embodiments of the invention.

In a further embodiment shown in FIG. 10, wherein the reservoir is a pouch 100, and when the reservoir is full, the pouch is confined by a solid surface 102 such as the inside of an outer hermetic enclosure or a molded plastic restrainer 104.

Figure 11:
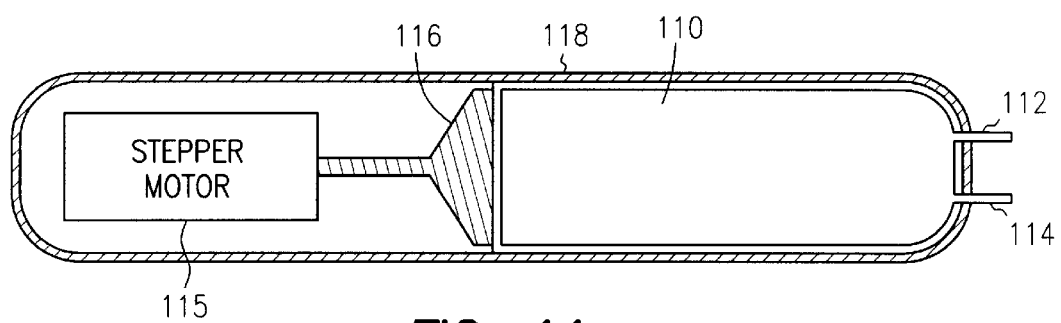
Figure 12:
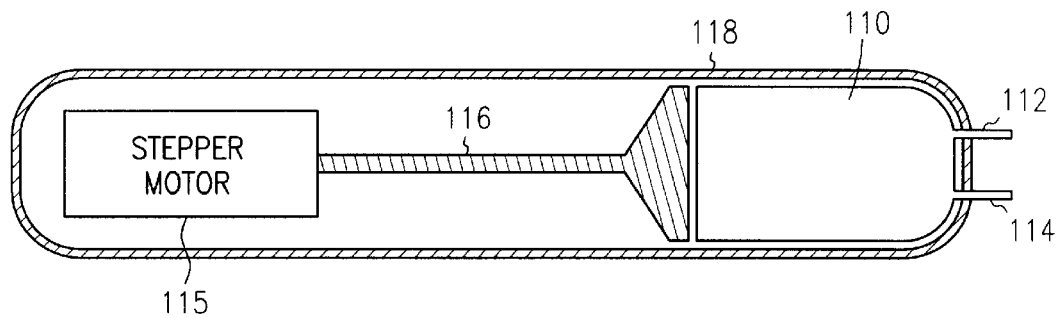

In a still further embodiment illustrated in FIG. 11, one end of a reservoir 110 has a fixed dimension and contains an outlet port 112 and a filling port 114, with the opposing end having a non-fixed dimension activated by a push rod or piston mechanism 116 to predictably collapse the pouch 118 while pushing the therapeutic agent out under constant pressure. As also shown in FIG. 11, the reservoir 110 is enclosed in a solid casing 118 and a drive or stepper motor 115 retains the therapeutic agent and to forces the agent through the outlet port 112. Thus, the pump is a diaphragm pump or piston pump that controls dosage volume by change in volume per stroke multiplied by the number of strokes. In FIG. 12, the pouch 110 is shown partially collapsed by piston mechanism 116.

Another embodiment provides that after an infusion cycle, the drive or stepper motor 115 reverses enough to release pressure on the therapeutic agent chamber and to maintain a neutral or slight negative pressure in relation to that of the surrounding anatomy.

Figure 13:
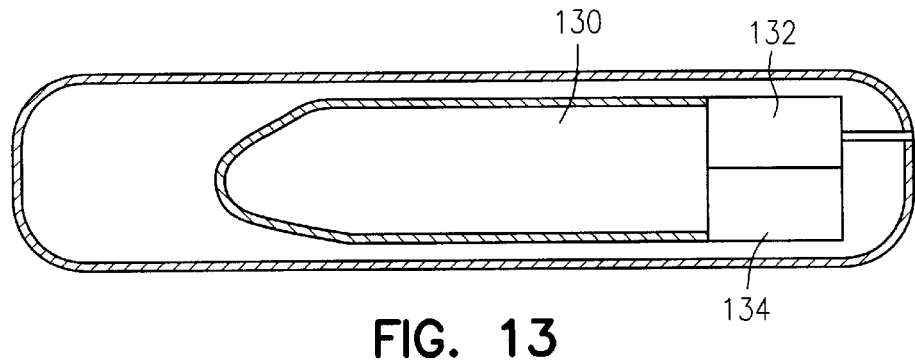
Figure 14:
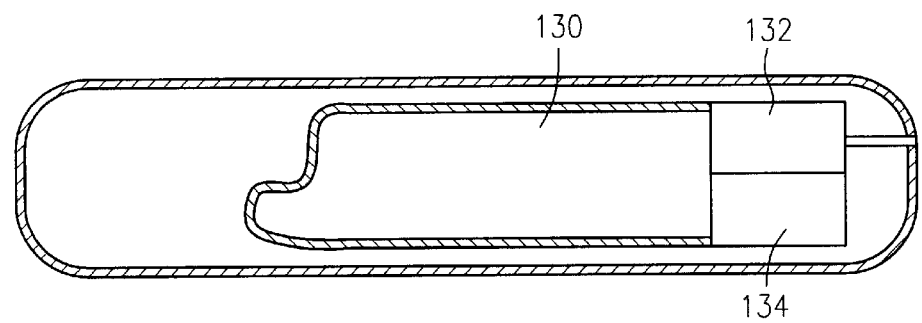

In yet still another embodiment shown in FIG. 13, a screw or impeller pump 132 is located at the fixed end of a reservoir 130 and withdraws the agent from the reservoir 130. In one such example embodiment, the reservoir 130 is a pouch or bladder and agent is pumped from the pouch, and the pouch collapses as it is emptied, maintaining the appropriate pressure/volume ratio inside the pouch and thereby preventing air from entering the pouch. In an example embodiment such as shown in FIG. 13 wherein the pump is a screw or impeller, it is for example driven by a stepper or microstepper motor 134 that is accurately controlled to regulate the dosage volume by number of rotations of the screw or impeller. In FIG. 14, the reservoir 130 is shown further deflated from its form in FIG. 13, as a result of agent being withdrawn.

Figure 15:
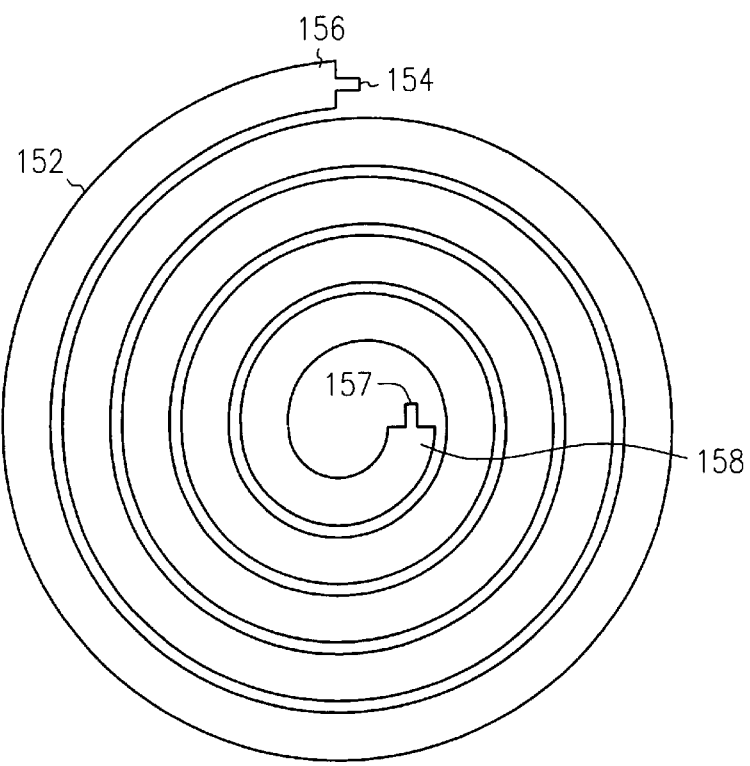

In one example embodiment of the apparatus shown in FIG. 15, the reservoir 150 is a square or round hollow, rigid tube 152 coiled to maintain a flat or specifically shaped profile of minimum surface area, and the reservoir is filled through an inflow valve 154 located at or near one end 156 of the tube, and the outflow port 157 is located at the opposite end of the tube 158 from the valve 154.

Figure 16:
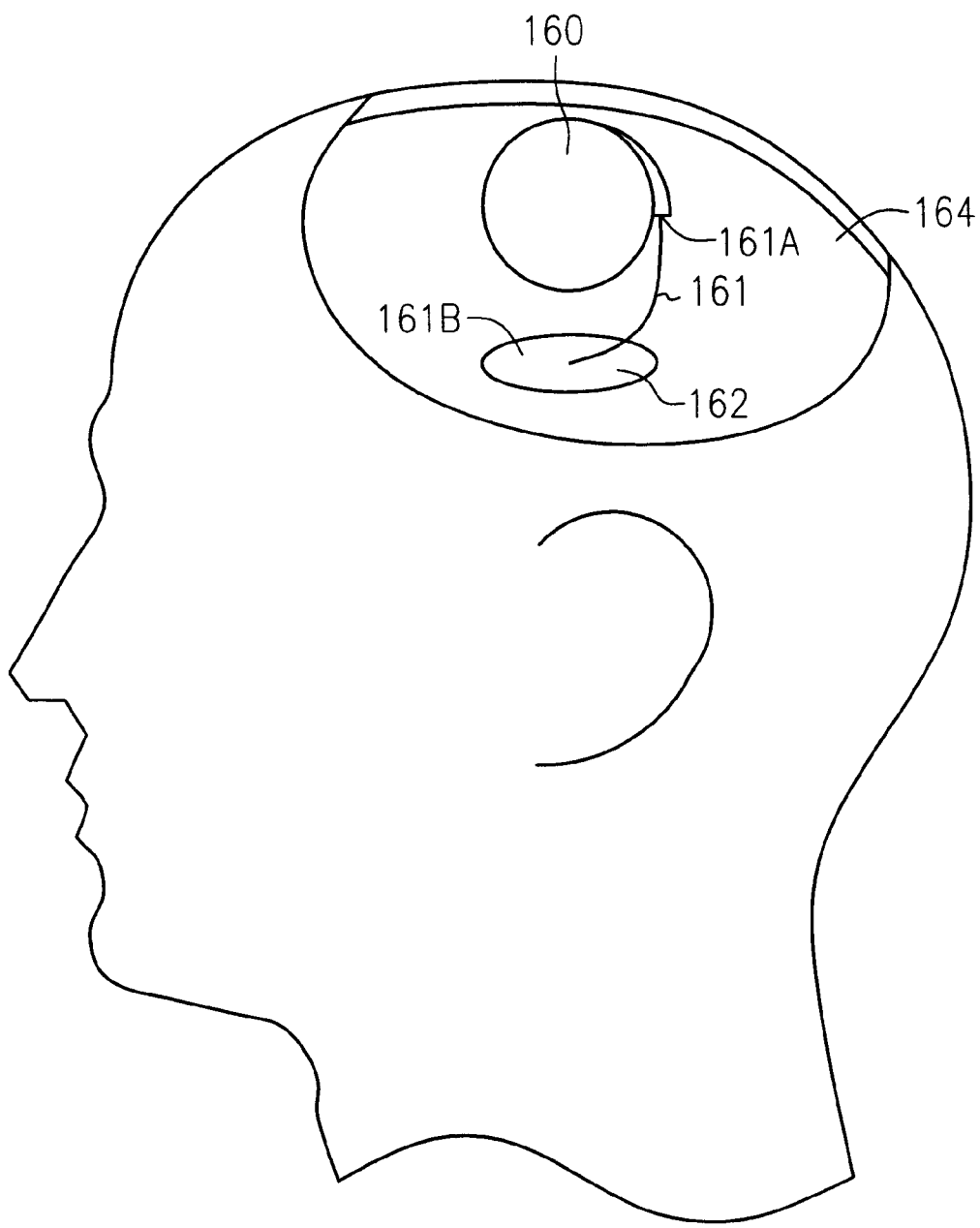
FIG. 16 shows an implanted system according to one embodiment of the invention.

According to still another embodiment shown in FIG. 16, the therapeutic agent is dispensed from the reservoir 160 to a location 162 in the brain 164 of the subject. Such dispensing is done in one example embodiment based on programmed parameters. Such programmed parameters are for example telemetered transcutaneously. Further, information may be telemetered transcutaneously to a device outside the subject's body. According to one such embodiment, the agent is dispensed using a fluid conduit 161 with a proximal end 161a coupled to receive agent from the reservoir 160 and a distal end 161b positioned in the brain 164 of the subject.

Figure 17:
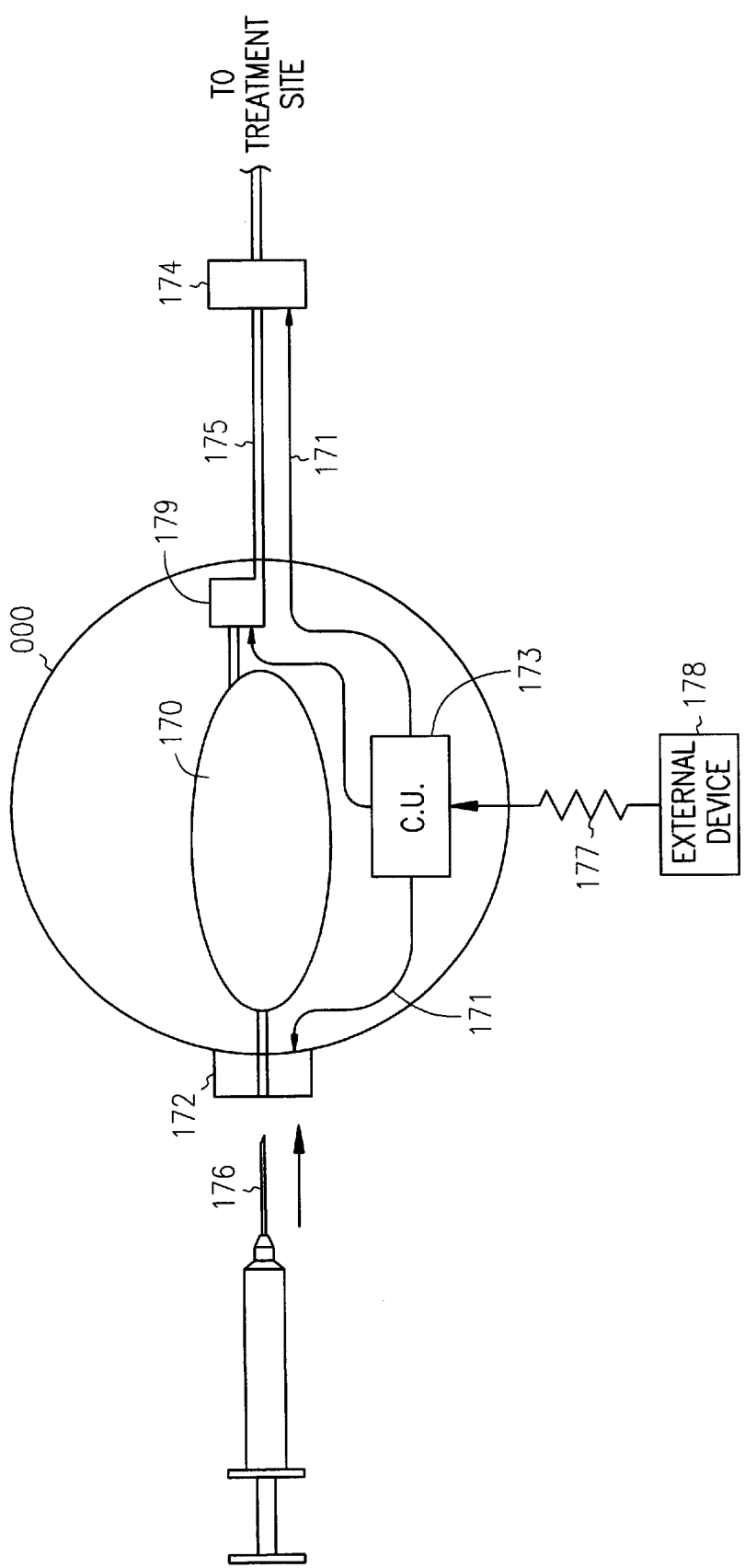
FIG. 17 shows an implanted unit having a telemetry control system according to one embodiment of the invention.

In still other embodiments for example shown in FIG. 17, a first valve 172 regulates the inflow and a second valve 174 regulates the outflow of agent from reservoir 170. Yet another embodiment provides that the inflow valve 172 is a mechanical valve displaced by a refill needle 176. In one example embodiment, the inflow valve 172 is an electronically controlled valve that is activated by an external device 178 through control unit 173 using telemetered signals 177 at the time of filling, and/or the outflow valve is electronically controlled and timed to the outflow cycle of the pump using control unit 173 and signals 177 telemetered by device 178. In this arrangement, for instance, the outflow valve 174 is a normally closed valve located at the distal end of a catheter or tube 175 carrying the therapeutic agent to a treatment site in the subject's body, and when therapeutic agent delivery is required, the valve 174 is electrically opened and remains open for a programmed period of time so that pump 179 can pump agent from reservoir 170 to the treatment site. According to yet one more embodiment, conductors 171 carrying control signals to the valve 174 are embedded in the sidewall of the catheter 175. In another embodiment, valve 174 is positioned at the proximal end of conduit 175 at the discharge port of the reservoir. According to one illustrative embodiment, the valve 172, pump 179, control unit 173, reservoir 170 and optionally valve 174 are mounted inside or integrated with a housing 169.

Figure 18:
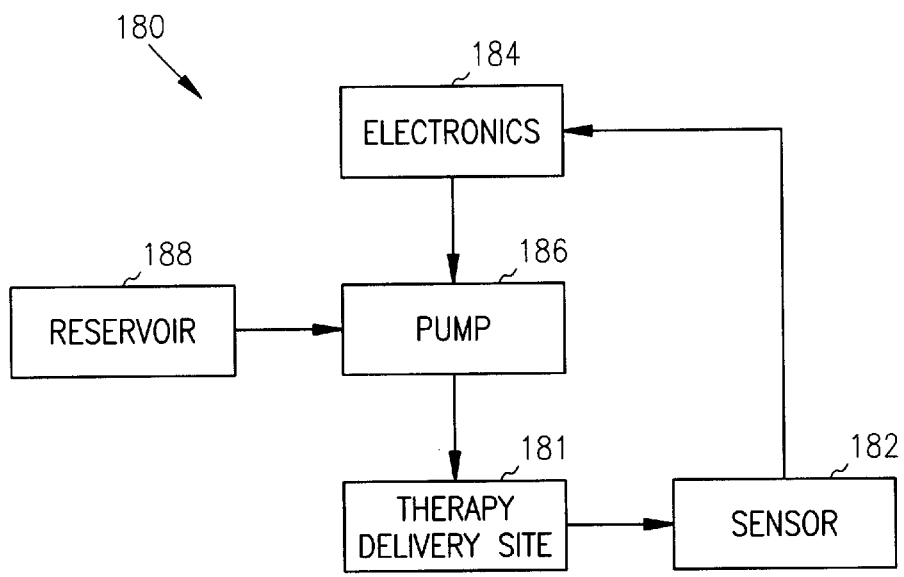
FIG. 18 shows a closed loop feedback system according to one embodiment of the invention.

In still another arrangement illustrated in FIG. 18, there is provided a closed loop sensory mechanism 180 that determines when to deliver a dosage of therapeutic agent and how much therapeutic agent dosage is appropriate. Sensor 182 senses delivery of the therapeutic agent to treatment site 181 and provides a feedback signal to electronics 184, which in turn controls the pump 186 to pump agent from reservoir 188 to site 181.

Figure 19:
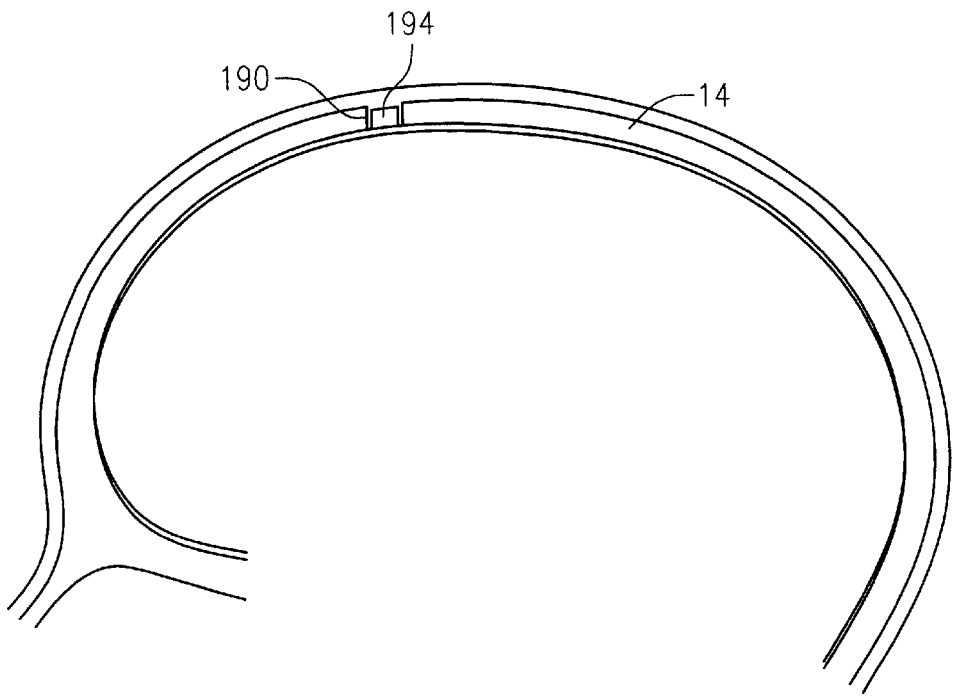
FIG. 19 shows an implanted unit according to one embodiment of the invention.

Yet another example embodiment illustrated in FIG. 19 provides for forming at least one cavity 190 in the cranium 14 of the subject, and placing at least a portion of a pump 194 in the cavity. In yet another example embodiment, the cavity 190 is a burrhole.

Figure 20:
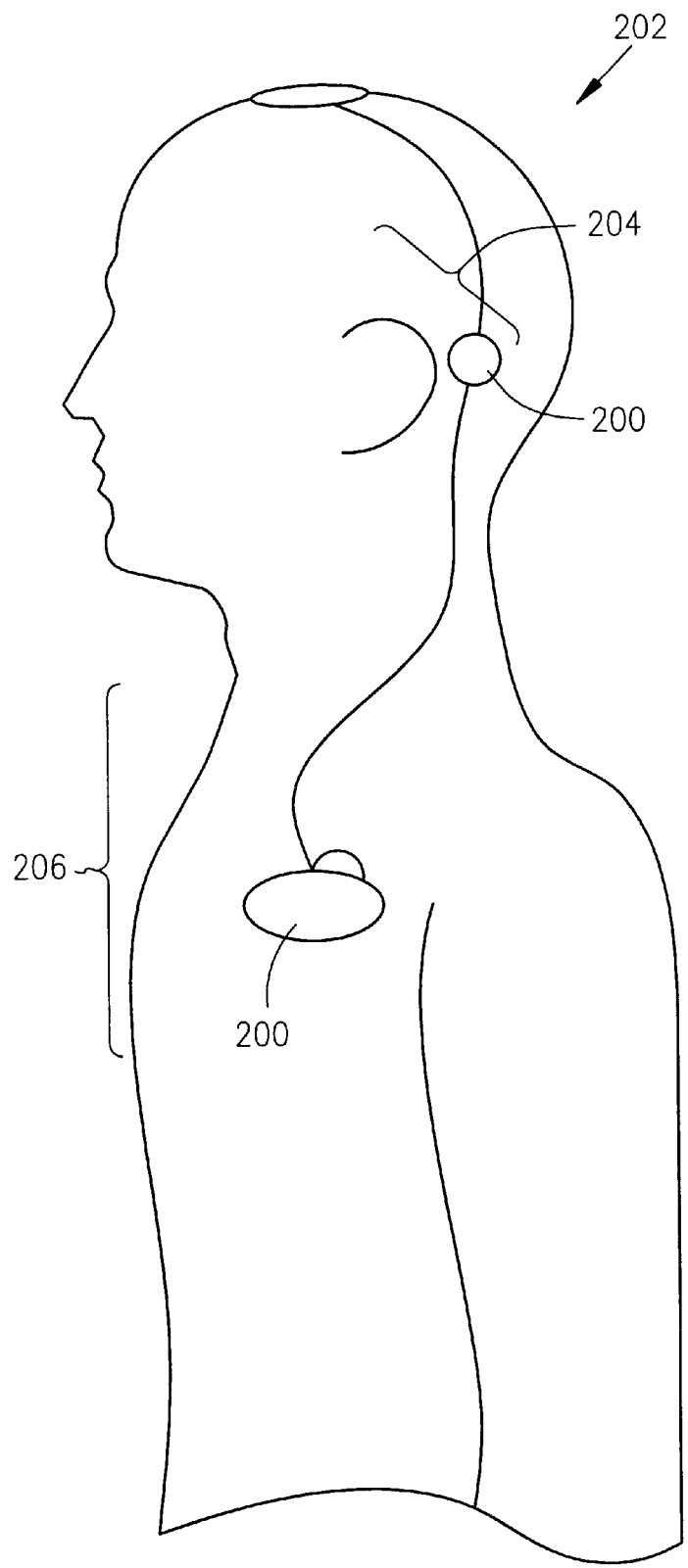
FIG. 20 shows two example deployments according to one embodiment of the invention.

Yet more example embodiments illustrated in FIG. 20 provide for positioning control electronics or a battery 200 for the pump inside the body 202 of the subject at a location other than the top of the head of the subject, such as under the skin behind the ear of 204 the subject, or alternatively (dotted lines) in the chest region 206 of the subject.

Figure 21:
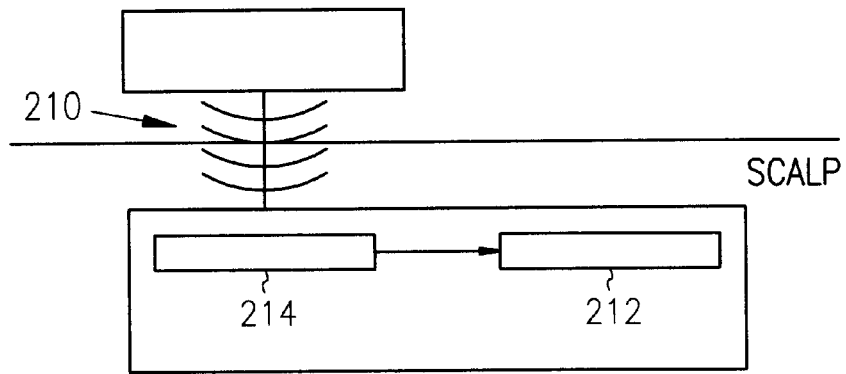
FIGS. 21–23 show power system configurations according to one embodiment of the invention.
Figure 22:
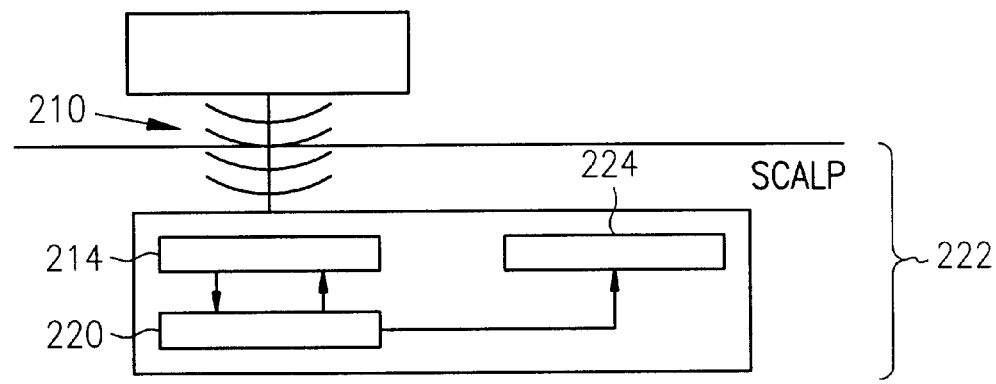

In still more embodiments as for example illustrated in FIGS. 21 and 22, power 210 is transmitted by RF energy to a pump 212 transcutaneously (FIG. 21) and received by a circuit 214 that converts the RF energy to power for the pump 212 or valve control, or as show in FIG. 22 an implanted power source 220 is retained within the subject's body 222, wherein the power source 220 powers a pump 224, and for example the power source is rechargeable. Such rechargeable power source is a rechargeable battery or, alternatively a storage capacitor. The rechargeable power source is recharged in this embodiment, for example, by transcutaneously transmitting power to the power source. In some operational modes, the therapeutic agent is pumped as an external power source is placed over the site of the pump and reservoir.

Figure 23:
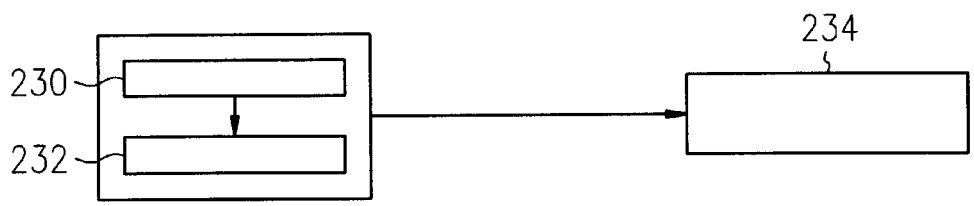

As illustrated in FIG. 23, still other embodiments provide that the power source 230 is integral with electronic circuitry 232 used to control a pump 234.

Figure 24:
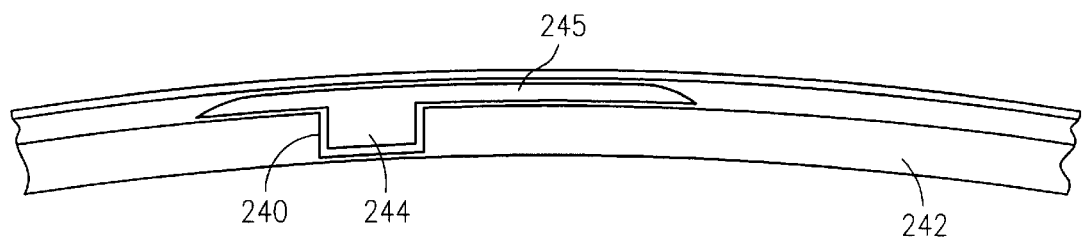
FIG. 24 shows an example implant unit according to one embodiment of the invention.

The apparatus of the invention further provides in one example arrangement as illustrated in FIG. 24, for forming at least one cavity 240 in the cranium of the subject 242, and placing at least a portion of the power source 244 in the cavity. As shown in FIG. 24, the power source is proximate or integral a reservoir housing 245. Alternatively, in another embodiment, the electronics are also mounted in the burr hole with the battery. The power source is a rectifier or battery.

Figure 25:
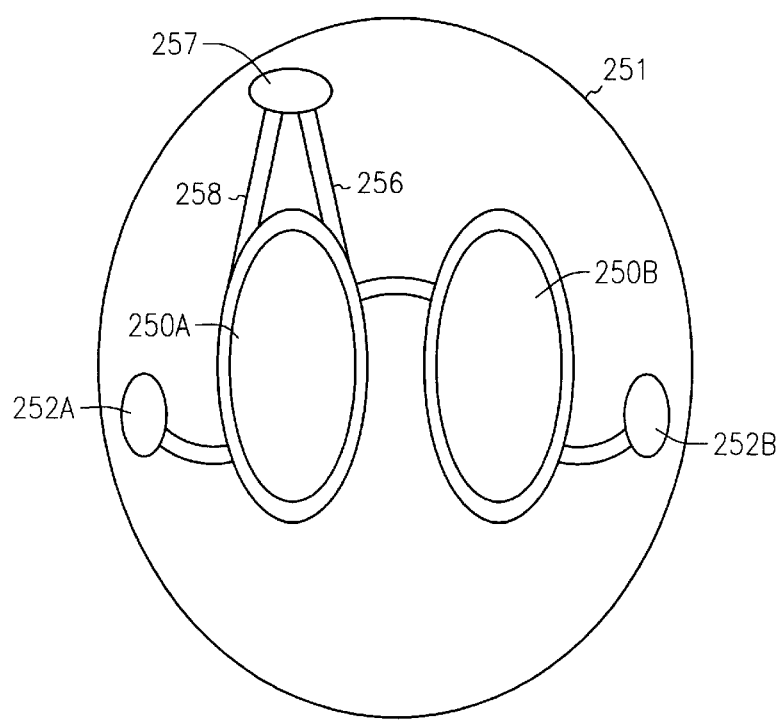
FIG. 25 shows a perspective view of an implanted multiple reservoir system according to one embodiment of the invention.

Referring to FIG. 25, there is illustrated in three dimensional schematic form an example embodiment showing a pair of reservoirs 250a and 250b positioned generally on the top of a subject's cranium, on either side of the crown, with each reservoir including a refill port 252a and 252b connected to each respective reservoir with a fluid conduit. The refill ports 252a and 252b are preferably positioned behind each ear such that a refill syringe can be inserted through the skin into the port without the requirement of shaving hair from the subject's scalp to obtain a clean entry path. The reservoirs are connected with a fluid conduit 254. A further fluid conduit 256 carries therapeutic agent from one of the reservoirs to a burrhole access into the subject's brain, and a catheter carries the therapeutic agent from the access point into the brain.

In yet more example embodiments of the apparatus, more than one cavities or burrholes are formed in a subject's cranium, and at least a portion of a pump is retained in one cavity and at least a portion of a power source for the pump in the other cavity.

Figure 26:
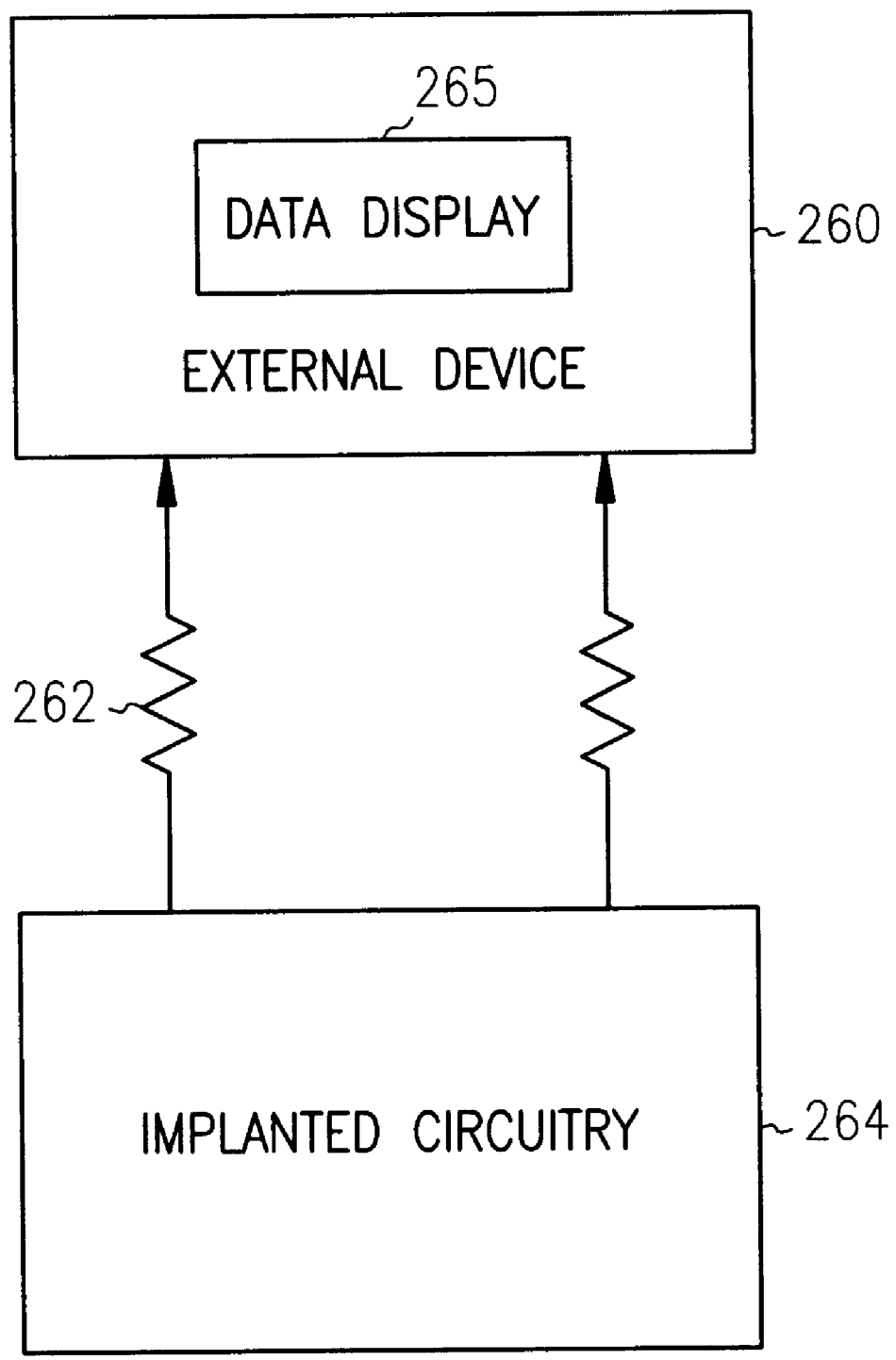
FIG. 26 shows a telemetry/control system according to one embodiment of the invention.

As illustrated in FIG. 26, an external device 260 is provided on one example embodiment to telemeter signals 262 into and out of implanted electronic circuitry 264. In such an example embodiment, the external device 260 reprograms the electronic circuitry 264 as necessary, and collects and displays data 265 as transmitted from the implantable device. Further, the external electronic device 260 in some embodiments signals the electronic circuitry 264 to cause an extra dose of therapeutic agent to be delivered upon demand by an operator. In some example configurations, the bidirectional transmitting provides signals to activate the circuitry within the implant device and relay status information from the circuitry 264 to outside the subject's body. Such signals include in some example cases starting energy and signal transmission either automatically by proximity of the external device to the implanted device or by a control activated by an operator.

According to one example embodiment of the invention, the dimensions are as follows, for implant under the scalp, are as follows:

Housing volume: approximately less than or equal to 50 cc.

Thickness (side profile) of housing: approximately 3–5 mm.

Thickness (side profile) of housing including for example electronicsibattery burrhole section(s): approximately 12–14 mm.

Maximum housing dimension in length or width: approximately 145 mm.

According to such example embodiment, the housing may enclose or house the reservoir and/or pump and/or other components such as the electonics and power source.

According to one illustrative embodiment, these parameters are the totals for both housings if more than one housing is used.

According to another example embodiment of the spinal reservoir/pumping invention, for implant in the back for use with spinal treatments, are as follows:

Housing volume: approximately less than or equal to 50 cc.

Thickness (side profile) of housing: approximately 5–10 mm.

Maximum housing dimension in length or width: approximately 110 mm. (including reservoir and/or pump and/or other components According to one illustrative embodiment, these parameters are the totals for both housings if more than one housing is used.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the invention. It is manifestly intended that this invention be limited only by the following claims and equivalents thereof.

We claim:

1. A method comprising:
    retaining a reservoir for a therapeutic agent between the galea aponeurotica and cranium of a subject; and
    pumping the therapeutic agent from the reservoir to a location in the subject's body with a pump.

2. A method according to claim 1 wherein the pump is selected from the group of: a screw, impeller, diaphragm, or piston type pump.

3. A method according to claim 1 wherein the pump is a screw or impeller type motor driven by a stepper or microstepper motor that is accurately controlled to regulate the dosage volume by number of rotations of the screw or impeller.

4. A method according to claim 1 wherein the pump is a diaphragm pump or piston pump that controls dosage volume by change in volume per stroke X number of strokes.

5. A method according to claim 4 further including controlling the flow of agent using a first valve to regulate the inflow and a second valve to regulate the outflow.

6. A method according to claim 5 further wherein the output valve is located at a discharge port of the pump, and opened electrically.

7. A method according to claim 1 further including a closed loop sensory mechanism that determines when to deliver a dosage of therapeutic agent and how much therapeutic agent dosage is appropriate.

8. A method according to claim 1 further including forming at least one cavity in the cranium of the subject, and placing at least a portion of the pump in the cavity.

9. A method according to claim 1 further including positioning the pump or electronics inside the body of the subject at a location other than the top of the head of the subject.

10. A method according to claim 1 further including positioning the pump or electronics under the skin behind the ear of the subject.

11. A method according to claim 1 further including positioning the pump or electronics in chest region of the subject.

12. A method according to claim 8 further wherein the burrhole stops short of penetrating the inner table of the calvaria so as to maintain an infection barrier to the brain.

13. A method according to claim 1 further including transmitting power to the pump transcutaneously.

14. A method according to claim 1 wherein the reservoir has a volume of approximately 50 cc or less.

15. A method according to claim 1 further including electronic circuitry operating the pump based on programmed parameters.

16. A method comprising retaining a reservoir for a therapeutic agent between the galea aponeurotica and cranium of a subject and further including using one or more electronic components adapted to control the dispensing of therapeutic agent from the reservoir to the subject's body.

17. A method according to claim 16 wherein the components or pump are enclosed in a fluid-tight enclosure and all components and connections are hermetically sealed against potential moisture related failures.

18. A method according to claim 16 further including forming at least one cavity in the cranium of the subject, and placing at least a portion of the components in the cavity.

19. A method comprising
    retaining a reservoir for a therapeutic agent between the scalp and cranium of a subject; and
    dispensing the therapeutic agent by pumping the therapeutic agent to a location in the subject's body with a pump.

20. The method according to claim 19, wherein the pump is selected from the group of a screw, impeller, diaphragm, or piston type pump.

21. A method according to claim 20, further including electronically controlling the dispensing of therapeutic agent from the reservoir to the subject's body.

* * * * *

UNITED STATES PATENT AND TRADEMARK OFFICE
CERTIFICATE OF CORRECTION

PATENT NO. : 6,726,678 B1
DATED : April 27, 2004
INVENTOR(S) : Nelson et al.

It is certified that error appears in the above-identified patent and that said Letters Patent is hereby corrected as shown below:

<u>Title page,</u>
Item [75], Inventors, delete "Randy Nelson," and insert -- Randal S. Nelson, --.

<u>Column 10,</u>
Line 51, delete "electonics" and insert -- electronics --.
Line 64, after "components" insert -- ) --.

Signed and Sealed this

Twenty-eighth Day of February, 2006

JON W. DUDAS
*Director of the United States Patent and Trademark Office*

UNITED STATES PATENT AND TRADEMARK OFFICE
CERTIFICATE OF CORRECTION

PATENT NO.       : 6,726,678 B1                                  Page 1 of 1
APPLICATION NO.  : 09/790982
DATED            : April 27, 2004
INVENTOR(S)      : Charles L. Truwit and Randal S. Nelson It is certified that error appears in the above-identified patent and that said Letters Patent is hereby corrected as shown below:

<u>Title page,</u>
Item [73], Assignee, add -- Regents of the University of Minnesota", MN (US) --.

Signed and Sealed this

Twentieth Day of June, 2006

JON W. DUDAS
*Director of the United States Patent and Trademark Office*